US008420361B2

(12) United States Patent
Reuter et al.

(10) Patent No.: US 8,420,361 B2
(45) Date of Patent: Apr. 16, 2013

(54) CLOSTRIDIUM SPOROSPHAEROIDES FOR THE TREATMENT OF BIOMASS

(75) Inventors: Monika Reuter, Altotting (DE); Vera Duchow, Laupheim (DE); Daniel Vater, Bad Muskau (DE)

(73) Assignee: Schmack Biogas GmbH, Schwandorf (DE)

(*) Notice: Subject to any disclaimer, the term of this patent is extended or adjusted under 35 U.S.C. 154(b) by 0 days.

(21) Appl. No.: 12/735,380

(22) PCT Filed: Jul. 7, 2009

(86) PCT No.: PCT/DE2009/075035
§ 371 (c)(1),
(2), (4) Date: Sep. 16, 2010

(87) PCT Pub. No.: WO2010/072219
PCT Pub. Date: Jul. 1, 2010

(65) Prior Publication Data

US 2011/0244542 A1 Oct. 6, 2011

(30) Foreign Application Priority Data

Dec. 23, 2008 (WO) ................ PCT/DE2008/075017
Mar. 7, 2009 (DE) ......................... 10 2009 003 587

(51) Int. Cl.
*C12P 5/02* (2006.01)
*C12P 1/04* (2006.01)
*C12N 1/20* (2006.01)

(52) U.S. Cl.
USPC ......................... 435/167; 435/170; 435/252.7

(58) Field of Classification Search .................. 435/167, 435/170, 252.7
See application file for complete search history.

(56) References Cited

U.S. PATENT DOCUMENTS

2008/0311640 A1* 12/2008 Cox et al. ...................... 435/168

FOREIGN PATENT DOCUMENTS

CA 2 258 254 A1 6/2000
WO WO 2006/056819 A 6/2006
WO WO 2006/119052 A 11/2006
WO WO 2007/052306 A 5/2007

OTHER PUBLICATIONS

Nielsen et al. "Bioaugmentation of a two-stage thermophilic (68 degrees C/55 degrees C) anaerobic . . . " Biotechnology and Bioengineering, vol. 97, No. 6, Aug. 2007.
"Uncultured Clostridiales bacterium clone 1099972248072 16S ribosomal RNA gene, partical sequence" Database EMBL [Online] Accession No. EF434352, Mar. 21, 2007.
Liu et al. "Characterization of microbial community in granular sludge treating brewery . . . " Water Research, Elsevier, Amsterdam, NL, vol. 36, No. 7, Apr. 1, 2002.
Krober et al. "Phylogenetic characterization of a biogas plant microbial community integrating clone library . . . " Journal of Biotechnology, vol. 142, No. 1, Jun. 1, 2009.
Sneath et al. "Bergey's manual of systematic bacteriology, vol. 2, Section 13: Endospore-forming . . . " 1986, pp. 1151, 1192-1193.

(Continued)

*Primary Examiner* — Rosanne Kosson
(74) *Attorney, Agent, or Firm* — Welsh Flaxman & Gitler LLC

(57) ABSTRACT

A method of treatment of biomass is described, characterized in that a microorganism of the species *Clostridium sporosphaeroides* is added to the biomass.

13 Claims, 4 Drawing Sheets

OTHER PUBLICATIONS

Quentmeier et al. "Characterization of Citrate . . . " Biosciences Information Service, Philadelphia PA, Database Biosis [Online] & Archives of Microbiology, vol. 141, No. 1, 1985, Bibliographic data only.

Wilde et al. "*Clostridium pascui* sp. nov., a new glutamate-fermenting sporeformer . . . " International Journal of Systematic Bacteriology, vol. 47, No. 1, Jan. 1997.

Stengl et al. "Betriebsstabilitat von Biogasanlagen" ETA Energie [Online] No. 3, 2007 URL:http://www.succidia.de/n_energie.html>.

Sneath et al. "Bergey's manual of systematic bacteriology, Endospore-forming Gram-positive rods and cocci" vol. 2, Jan. 1, 1986, pp. 1154, 1187-1188.

Hu et al. "Changes in microbial community composition following treatment . . . " Environmental Progress & Sustainable Energy, vol. 28, No. 1, Apr. 1, 2009.

Sneath et al. "Bergey's manual of systematic bacteriology, Endospore-forming Gram-positive rods and cocci" vol. 2, Jan. 1, 1986, pp. 1118, 1123-1124, 1133.

Van Heerden et al. "Microbial, chemical and physical aspects of citrus waste composting" Bioresource Technology, Elsevier BV, GB, vol. 81, No. 1, Jan. 1, 2002.

Ryckeboer et al. "Microbiological aspects of biowaste during composting in a monitored compost bin" Journal of Applied Microbiology, Oxford GB, vol. 94, No. 1, Jan. 1, 2003.

* cited by examiner

CLOSTRIDIUM SPOROSPHAEROIDES FOR THE TREATMENT OF BIOMASS

TECHNICAL FIELD

The invention relates to a method of treatment of biomass using a microorganism of the species *Clostridium sporosphaeroides*.

PRIOR ART

Biofuels are mainly obtained by fermentation of plant substrates by means of yeasts, bacteria or fungi. The liquid energy carriers produced, especially bioethanol, can then be used as fuel in suitable furnaces or as fuel or fuel additives in engines of motor vehicles or engines for producing electricity and heat. The biomass is thus converted to an easily transportable liquid energy carrier with relatively high energy density, which is then widely suitable for universal application.

Mostly locally available plants with a high content of sugar or starch are used as raw materials for the production of liquid biofuels. In Europe, these are mainly maize and cereal grains and sugar beet; in North America, maize; and, in Latin America, sugar cane or molasses. Other energy plants are also considered, such as sorghum, triticale or cassava (manioc). At present maize grain and cereal grain are used in particular as starting materials in the liquefaction of biomass. Owing to the increasing shortage of raw materials, higher raw material prices, a situation in which there is competition for plants, which are used both as food for humans and animals and for energy production, an improved $CO_2$ balance and conservation of resources, there are now increasing efforts to use not only the grains of maize and cereals, but instead employ the whole plant for energy production or use plants that do not require intensive agricultural management such as switchgrass or zebra grass. The biofuels produced from these raw materials are so-called "second generation" fuels. Increased utilization of favorable plant residues such as straw, plant waste products from the timber industry, or garden and landscape management is also desirable.

To ensure efficient fermentation of biomass, the plant material used as raw material and, in particular, the organic dry matter (oDM) contained therein, must be released for subsequent utilization. This takes place by hydrolysis of the organic dry matter, which is equivalent to liquefaction of the organic dry matter. Ethanol, or some other biofuel, is then produced from the liquid biomass substrate by fermentation. However, high energy efficiency is not achieved with the present techniques, in particular owing to inadequate liquefaction and therefore utilization of the raw material.

In the production of bioethanol, ethanolic fermentation is mainly effected with added yeasts, which convert glucose to ethanol. Depending on the substrate, a relatively high proportion of sugar is already present (e.g. in the case of molasses) or higher-molecular substrates such as starch, cellulose or hemicellulose (e.g. in the case of cereals, straw, use of whole plants) must first be cleaved enzymatically or chemically, so that alcoholic fermentation can take place. Microorganisms, in particular bacteria, are mainly responsible for this hydrolytic substrate decomposition, which is also equivalent to liquefaction.

If the conversion of organic raw materials is to lead to a gaseous energy carrier rather than a liquid biofuel, biogas installations are used. In biogas installations, methane is produced by a microbial process for degradation of organic substances. The biogas is, in this case, formed in a multistage process of fermentation or digestion through the activity of anaerobic or microaerophilic microorganisms, i.e. with exclusion of air.

From the chemical standpoint, the organic material used as fermentation substrate has a high-molecular weight structure, which in the individual process steps of a biogas plant is broken down by the metabolic activity of the microorganisms to low-molecular weight building blocks. Until now, however, the populations of microorganisms that are active in the fermentation of the organic fermentation substrate have not been characterized sufficiently.

According to the present state of knowledge, there are four biochemical metabolic processes that take place successively, but also in parallel and interacting with one another, leading to the degradation of organic fermentation substrates to the end products methane and carbon dioxide: hydrolysis, acidogenesis, acetogenesis and methanogenesis.

In hydrolysis, high-molecular weight organic compounds, often present in particulate form, are converted by exoenzymes (e.g. cellulases, amylases, proteases, lipases) of fermentative bacteria to soluble cleavage products. For example, fats are broken down to fatty acids, carbohydrates, e.g. polysaccharides, to oligo- and monosaccharides, and proteins to oligopeptides and/or amino acids. The gaseous products that are also formed consist mainly of carbon dioxide.

Facultative and obligate anaerobic bacteria, often identical to the hydrolyzing bacteria, metabolize, in acidogenesis, the hydrolysis products (e.g. mono- and disaccharides, di- and oligopeptides, amino acids, glycerol, long-chain fatty acids) intracellularly to short-chain fatty acids or carboxylic acids, for example butyric, propionic and acetic acid, to short-chain alcohols such as ethanol, for example, and to the gaseous products hydrogen and carbon dioxide.

In the subsequent acetogenesis, the short-chain fatty acids and carboxylic acids formed in acidogenesis and the short-chain alcohols are taken up by acetogenic bacteria and, after β-oxidation, are excreted again as acetic acid. By-products of acetogenesis are $CO_2$ and molecular hydrogen ($H_2$).

The products of acetogenesis such as acetic acid, but also other substrates such as methanol and formate, are converted by methane-forming organisms to methane and $CO_2$ in the obligate, anaerobic methanogenesis. The resultant $CO_2$, as well as $CO_2$ formed during the other process steps, e.g. hydrolysis, can once again also be converted by microorganisms to methane, with the $H_2$ that has formed.

Increasing the yield of end products from a given amount of educts is, as with any chemical reaction, also both in the case of liquefaction of biomass and in the production of biogas, an urgent objective of process control. The largest possible amount of liquid organic compounds or the largest possible amount of methane should be formed from a given amount of biomass.

In 2005, the Fachagentur Nachwachsende Rohstoffe (Agency for Renewable Resources) published the results of a biogas measurement program ("Results of the biogas measurement program", 2005, Publ. Fachagentur Nachwachsende Rohstoffe e.V., Gülzow), in which various biogas installations were compared. This measurement program provides a representative cross section of the present wide range of installations, as biogas installations of various designs, from various manufacturers and installations operating with various materials were included. The measured overall volumetric loadings of the biogas installations investigated were in the range from 0.45 kgoDM/m³d (multistage installations) to 5.7 kgoDM/m³d (single-stage installations). For the majority of single-stage and multistage installations the volumetric loading was between 1 and 3 kgoDM/m³d.

The volumetric loading of a fermenter is understood as the amount of substrate supplied to the fermenter, which is stated in kilograms of organic dry matter per cubic meter of fermenter volume per day. The amount of biogas produced is strongly dependent on the volumetric loading of the fermenter, with an increasing amount of biogas being produced with increasing volumetric loading. A high volumetric loading thus makes the process of biogas production increasingly economically profitable, but conversely leads to increasing destabilization of the biological processes of fermentation.

Increasing the volumetric loading is one possibility for operating a biogas plant more efficiently. In this case, biogas production is increased by slowly increasing the feed in oDM per day. High volumetric loadings of over 6 kgoDM/m$^3$d have so far not been used in practice. The objective in plant operation is to operate a plant economically. The stability of the biological process is then paramount, as plant failure is extremely costly.

In order to achieve this process stability, the existing plants are operated with small volumetric loadings, but this necessitates a correspondingly large fermentation volume for efficient operation. As a result, the initial investment is increased by additional building costs. With high volumetric loadings, owing to greater loading of the existing biocoenosis in the fermenter with organic material mainly in the form of solids, there is continuous thickening of the fermenter contents. This is caused by increasing dry matter content and incomplete conversion of the biomass to biogas.

Substrates for biogas production have proportions of dry matter in the range from 5% to 90%. For wet fermentation processes, for which pumpable substrates are required, substrates can be used with a proportion of dry matter up to about 35 to max. 40%. As substrates with a higher proportion of dry matter, in particular a higher proportion of organic dry matter, generally provide a higher energy content, these would preferably be used. In this case, however, there are also higher costs through increased energy consumption in pumping and stirring and higher additional costs through wear or repair of pumps, stirrers etc. with high viscosity or a high dry matter content. If substrate dilution is necessary owing to a high dry matter content, there are additional water supply and sewerage costs and technical equipment for water supply, recovery or wastewater treatment.

In continuous operation, an increasing proportion of dry matter leads increasingly to problems with stirrability and pumpability of the fermenter contents. With further increase in dry matter content, this thickening leads to instability of the biocoenosis and thus to extensive or even complete cessation of the biological processes and therefore also of gas production, which is called "fermenter crash". To prevent thickening, the fermenter contents can be made more liquid by adding liquids, for example water or slurry. The problem here is the legal terms of reference (EEC), which for receipt of the dry fermentation bonus do not permit addition of substances having a lower proportion of dry matter than on average 30%. Therefore it is seldom possible to liquefy the fermenter material by adding more liquid.

Taking into account, in addition to the above considerations, the shortage of the resource fresh water, liquefying the fermenter contents by adding water is ruled out. Slurry as liquefying substance is on the one hand connected with high costs for equipment, and on the other hand it is not available everywhere and moreover is of variable quality. Furthermore, if slurry is used, depending on the state or country, a sanitation stage is required after the fermentation process for legal reasons, before the fermentation residue can be returned to the field.

There is therefore still a need for methods for the treatment of biomass, in particular more efficient methods of liquefaction of biomass for the production of biofuels and methods for production of biogas, which give an increased yield of biogas compared with the prior art.

SUMMARY OF THE INVENTION

A method of improving the production of biomethane, comprising the step of adding a microorganism of the species *Clostridium sporosphaeroides* in a form of a culture of microorganisms to a biomass, with the microorganism of the species *Clostridium sporosphaeroides* accounting for at least 1% of the total number of microorganisms present in the culture, thereby enhancing a production of the biomethane in the biomass. At about the same time as addition of the microorganism of the species *Clostridium sporosphaeroides*, an additional biomass is added to the fermentation reactor, and the volumetric loading in the fermentation reactor is increased continuously by continuous addition of the biomass.

DEFINITIONS

The term "biofuel" means, within the scope of the present invention, a liquid or gaseous fuel or energy carrier, which is produced from biomass. Biofuels are used for the operation of internal combustion engines both for mobile applications (e.g. motor vehicles) and stationary applications (e.g. production of electrical and thermal energy in a cogenerating power station). Examples of biofuels are biodiesel, bioethanol, biomethanol, biokerosene, biohydrogen or biogas.

The term "bioethanol" means, within the scope of the present invention, ethanol that has been produced by alcoholic fermentation from biomass as renewable carbon carrier or biodegradable fractions of wastes. It is used at various concentrations as addition to mineral oil fuels such as biodiesel or biofuel.

The term "biogas" means, within the scope of the present invention, the gaseous product from the anaerobic biological degradation of organic substrates. As a rule it contains approx. 45-70% methane, 30-55% carbon dioxide, and small amounts of nitrogen, hydrogen sulfide and other gases.

The terms "fermentation" or "fermenting" comprise, in the sense of the present invention, both anaerobic and aerobic metabolic processes, which under the action of microorganisms in a technical process can lead to the production of a product, e.g. biogas, from the supplied substrate. (The German term "Gärung"—also translated as "fermentation"—is more restricted in meaning, as it applies exclusively to anaerobic processes.)

"Fermenter" means, within the scope of the present invention, the vessel in which the microbiological degradation of the substrate takes place, with simultaneous formation of biogas. The terms "reactor", "fermenting vessel" and "septic tank" are used synonymously.

The terms "fermentation substrate" or "substrate" mean, within the scope of the present invention, organic and biodegradable material, which is added to the fermenter for fermentation. Substrates can be renewable raw materials, organic manure, substrates from the agricultural processing industry, communal organic residues, abattoir wastes or summer pruning. Examples of these substrates are maize silage, rye silage, sugar-beet chips, molasses, grass silage, cattle or pig slurry, cattle, pig, chicken or horse dung, brewer's grains, apple, fruit or vine residues, grain, potato or fruit stillage, organic waste from the organic waste bin, food residues, market wastes, fat from fat separators, rumen contents, pig stomach contents. The terms "fermentation substrate" and "substrate" are used synonymously.

The term "fermentation residue" or "wash" means the residue from biogas production, which leaves the fermenter and is often stored in a separate vessel.

"Volumetric loading" means, within the scope of the present invention, the amount of organic dry matter (oDM) in kg supplied to the fermenter per day and per cubic meter ($m^3$) of working volume.

"Organic dry matter" (oDM) means, within the scope of the present invention, the water-free organic fraction of a mixture after removing the inorganic fraction and drying at 105° C. As a rule the proportion of dry matter is stated as a percentage of the substrate.

The term "dwell time" means, within the scope of the present invention, the average residence time of the substrate in the fermenter.

The term "specific biogas yield" or "specific methane yield" means, within the scope of the present invention, the amount of biogas or methane produced (stated in standard cubic meters $Nm^3$ of gas produced) divided by the amount (as a rule per tonne t) of organic dry matter or substrate used.

The term "space-time yield" represents the amount of biogas produced in standard liters (Nl) standardized to one liter of fermentation volume. This quantity provides better comparability of the gas output from different plants.

The term "nucleotide sequence" comprises both the DNA sequence and the corresponding RNA sequence. RNA sequences stated in the invention using the bases A, U, C, G also relate for example to the corresponding DNA sequences using the bases A, T, C, G and vice versa.

The nucleotide sequence of a microorganism is determined using a standardized process, by which the individual nucleotides of the DNA or RNA of the microorganism can be identified very accurately. Despite the great accuracy of sequencing methods, in a sequence there may often be individual positions for which the nucleotide present at a particular position could not be determined with sufficient accuracy. In such cases, within the scope of the present invention the letter "N" is shown in the nucleotide sequence. Hereinafter, if the letter "N" is used in a nucleotide sequence, then this stands as an abbreviation for each conceivable nucleotide, thus for A, U, G or C in the case of a ribonucleic acid or for A, T, G or C in the case of a deoxyribonucleic acid.

The term "nucleotide mutation" as used here means a change of the initial nucleotide sequence. Individual nucleotides or several nucleotide sequences following one another directly or interrupted by unchanged nucleotides can be removed (deletion), added (insertion or addition) or replaced with others (substitution). The term also includes any possible combination of the aforesaid individual changes.

The term "deletion" as used here means the removal of 1, 2 or more nucleotides from the particular starting sequence.

The term "insertion" or "addition" as used here means the addition of 1, 2 or more nucleotides to the particular starting sequence.

The term "substitution" as used here means the exchange of a nucleotide present in a particular position with another one.

The term "microorganism" means microscopically small organisms, which are as a rule unicellular (protozoa), but can also be multicellular (metazoa). Examples of microorganisms are bacteria, microscopic algae, fungi or protozoa.

The designations "genus" of microorganisms, "species" of microorganisms and "strain" of microorganisms mean, within the scope of the present invention, the corresponding fundamental category of biological taxonomy, in particular the phylogenetic classification. Genera, species and strains of microorganisms are identified and differentiated by, among other things, their RNA sequences. A given genus, a given species or a given strain includes not only microorganisms with a quite particular RNA sequence, but also to a certain extent their genetic variants, with the genetic variance increasing in the order strain, species, genus.

The definition of a "species" of a bacterium is in a process of scientific change and is neither completed, nor are the various concepts undisputed. In the present invention, "species" means the concept of species that is based on genomic and phylogenetic analyses and is described in Staley's review (Philos. Trans. R. Soc. Lond. B. Biol. Sci., 2006, 361, 1899-1909). It is most generally recognized that two bacterial species having more than 70% DNA-DNA hydridization or more than 94% average nucleotide identity (ANI) belong to the same species, or two species that have less than 97% identity of the 16S rRNA are to be assigned to two different species.

The term "culture" means in this context a collection of microorganisms under created conditions, which ensure the growth or at least the survival of the microorganisms. For bacteria these are for example enrichment cultures or pure cultures, liquid cultures as well as cultures on solid media such as culture medium, but also permanent cultures such as deep-frozen glycerol cultures, immobilized cultures such as gel cultures for example, or highly concentrated cultures such as cell pellets.

The term "pure culture" of a microorganism means the progeny of a single cell. This is isolated by a multistage process from a mixture of different microorganisms. The multistage process comprises separating an individual cell from a cell population and requires that the colony arising from the cell through growth and cell division is also kept separate from other individual cells or colonies. By carefully separating a colony, resuspending in liquid and repeated streaking, pure cultures of microorganisms can be obtained as required. The isolation of a pure culture can also take place in liquid nutrient media, provided the desired organism is numerically preponderant in the starting material. By serial dilution of the suspension in the nutrient solution, a state is finally reached where there is just one cell left in the last dilution stage. This cell then forms the basis for a pure culture. The explanation of the term "pure culture" and methods of production thereof are given in "Allgemeine Mikrobiologie" ("General microbiology") by Hans G. Schlegel, 7th revised edition, 1992, Georg Thieme Verlag, p. 205, reference being made to its entire contents.

The term "mixed culture" means a mixture of different microorganisms. Natural populations of microorganisms are as a rule mixed cultures. Mixed cultures can, however, also be produced artificially, e.g. by combining several pure cultures.

DETAILED DESCRIPTION OF THE INVENTION

The problem to be solved by the invention is to provide a method of treatment of biomass that gives an increased yield of utilizable biofuels compared with the prior art.

This problem is solved according to the invention by the method of treatment of biomass according to claim 1. Further advantageous details, aspects and embodiments of the present invention can be seen from the dependent claims, the description and the examples.

The present invention offers a method of treatment of biomass. A microorganism of the species *Clostridium sporosphaeroides* is added to the biomass.

Preferably, the method of treatment of biomass is a method of liquefaction of biomass. The use or the occurrence of microorganisms of the species *Clostridium sporosphaeroides* in the treatment of biomass or the production of biogas was not previously known. Surprisingly, however, it has been found that by adding microorganisms of the species *Clostridium sporosphaeroides* to a biomass substrate, the viscosity of the substrate can be reduced considerably. The use of microorganisms of the species *Clostridium sporosphaeroides* leads to a markedly intensified liquefaction of the biomass and in consequence to a marked improvement of the operational efficiency of plants for the production of biofuels.

Also preferably, the method of treatment of biomass is a method of production of biogas from biomass. It was found, surprisingly, that by adding microorganisms of the species *Clostridium sporosphaeroides* to the fermentation substrate, both the volumetric loading of the fermenter can be increased and the amount of biogas formed is increased considerably. As was shown in experimental investigations, addition of a microorganism of the species *Clostridium sporosphaeroides* brings about an increase in the volumetric loading of a fermenter by up to more than 50%, without the fermentation process becoming unstable. In parallel with the increased volumetric loading, the amount of biogas formed is increased considerably. There is also an increase in the specific yield of biogas, as far more of the organic dry matter is degraded than without addition of microorganisms of the species *Clostridium sporosphaeroides*. Owing to the increased degree of degradation, a greatly increased specific gas yield can be achieved, with improved substrate utilization. Moreover, by adding microorganisms of the species *Clostridium sporosphaeroides*, the dwell time of the fermentation substrate in the fermenter can be shortened considerably at constant gas yield, which also makes it possible to increase the volumetric loading. The use of microorganisms of the species *Clostridium sporosphaeroides* therefore leads to a dramatic improvement of the operational efficiency of biogas installations.

A possible explanation of the beneficial properties of the microorganisms of the species *Clostridium sporosphaeroides* is an increased rate of hydrolysis due to their metabolic activity, so that as a result of the metabolic activity a proportion of the difficultly degradable organic substances present (e.g. cellulose, hemicellulose) is converted to soluble acids and $CO_2$. Cellulose is insoluble in water and aqueous solutions, therefore degradation of cellulose in the fermentation process leads to liquefaction. The stirrability and pumpability of the material are maintained, as the dry matter content no longer increases. This makes constant thorough mixing of the material possible, with better withdrawal of gas from the process.

Owing to the increased degradative or metabolic performance of microorganisms of the species *Clostridium sporosphaeroides*, in the hydrolysis stage there is liquefaction of the fermenter material, but without observing acidification, or impairment of the methane content of the resultant biogas. The volumetric loading is greatly increased and the stability of the process is improved.

According to the invention, addition of microorganisms of the species *Clostridium sporosphaeroides* thus provides a method that ensures increased stability of the fermentation process and in which liquefaction of the fermentation substrate takes place. The liquefaction of substrate through the degradation of insoluble constituents can also be utilized for the production of biofuel from biomass.

According to a preferred embodiment of the present invention, a microorganism of the species *Clostridium sporosphaeroides* is added in the form of a culture of microorganisms, which consists predominantly of a microorganism of the species *Clostridium sporosphaeroides*. In fermentation substrates of biogas installations, microorganisms of the species *Clostridium sporosphaeroides* were only detected in minute traces of less than a $10^{-4}$% fraction of the total number of microorganisms present. As the number isolated from naturally occurring microorganisms is not as a rule sufficient for the addition of microorganisms, usually they are multiplied in the form of a culture. It is found in practice that it is simplest to add microorganisms to the fermentation substrate of a fermenter directly in the form of a culture of microorganisms.

The culture of *Clostridium sporosphaeroides* can be added in the form of a culture suspension, in the form of dry, freeze-dried or moist cell pellets or also in the form of spore suspensions, spore preparations or dry, freeze-dried or moist spore pellets.

As the various beneficial effects on the fermentation process already mentioned are connected with the species of microorganism *Clostridium sporosphaeroides*, this species of microorganisms should be present in the added culture in an amount greater than occurs naturally. Of course, mixed cultures of any composition can be used for the addition. The only precondition is that the species *Clostridium sporosphaeroides* is present in an enriched amount relative to what occurs naturally.

Mixed cultures of microorganisms of the species *Clostridium sporosphaeroides* with microorganisms of the species *Clostridium sartagoformum* and/or *Paenibacillus macerans* are preferred. Mixed cultures of microorganisms of the strain *Clostridium sporosphaeroides* SBG3 with microorganisms of the strains *Clostridium sartagoformum* SBG1a and/or *Paenibacillus macerans* SBG2 are especially preferred. Microorganisms of the species *Clostridium sartagoformum* and *Paenibacillus macerans* have, with reference to the treatment of biomass, similar properties as microorganisms of the species *Clostridium sporosphaeroides*, and are therefore eminently suitable for use in the treatment of biomass. Microorganisms of the species *Clostridium sartagoformum* and *Paenibacillus macerans* can therefore also be used in the methods and applications described here for the treatment of biomass.

Microorganisms of the species *Clostridium sporosphaeroides* are preferably added in the form of cultures of microorganisms to the fermentation substrate, with the cultures of microorganisms consisting mainly of microorganisms of the species *Clostridium sporosphaeroides*. If, along with determination of the number of microorganisms of the species *Clostridium sporosphaeroides*, the total number of microorganisms is also determined, then the proportion of microorganisms of the species *Clostridium sporosphaeroides* in the culture can be stated as a percentage. Microorganisms of the species *Clostridium sporosphaeroides* are the preponderant species of microorganisms in a mixed culture when they have the highest percentage proportion among the various species of microorganisms present in the mixed culture.

The composition of the microbial populations in the various fermentation substrates and the development of the composition of organisms during the fermentation process is for the most part unknown, but is very variable and is subject to a complicated dynamic process, which is also influenced by the particular process conditions. For determination of the microbial composition and the total number of microorganisms in a fermentation substrate, as well as determination of the proportions of various species of microorganisms in the fermentation substrate, various methods are known by a person skilled in the art, and are described for example in the review article by Amann et al. (Microbiol. Review. 59, 143-169, 1995).

A preferred method of determination of the composition of microorganisms independently of prior cultivation of the microorganisms is, for example, the preparation of an rDNA clone library (e.g. based on 16S rRNA) after nucleic acid extraction and PCR, which can then be sequenced. By means of this clone library, for example by in-situ hybridization with specific fluorescence-labeled oligonucleotide probes, the composition of the microbial population in the fermentation substrate can be determined. Suitable rRNA-based oligonucleotide probes are known from the aforementioned review or can be found for example by means of probeBase (Loy et al., 2003, Nucleic Acids Res. 31, 514-516. Loy et al., 2007. Nucleic Acids Res. 35: D800-D804) or the ARB software package (Ludwig et al., Nucleic Acids Research. 2004, 32, 1363-1371). A quantitative determination of the proportion of individual microorganisms in the total population can be carried out in a suitable way with the methods quantitative Dot Blot, in-situ hybridization or whole cell hybridization.

According to preferred embodiments of the present invention the microorganism *Clostridium sporosphaeroides* accounts for at least $10^{-4}$% of the total number of microorganisms present in the culture added to the fermentation substrate. Especially preferably the microorganism *Clostridium sporosphaeroides* accounts for at least $10^{-2}$% of the total number of microorganisms present in the culture and especially preferably the microorganism *Clostridium sporosphaeroides* accounts for at least 1% of the total number of microorganisms present in the culture.

According to further preferred embodiments the microorganism *Clostridium sporosphaeroides* accounts for at least 10% of the total number of microorganisms present in the culture, especially preferably the microorganism *Clostridium sporosphaeroides* accounts for at least 50% of the total number of microorganisms present in the culture and especially preferably the microorganism *Clostridium sporosphaeroides* accounts for at least 90% of the total number of microorganisms present in the culture.

According to a quite especially preferred embodiment, a pure culture of a microorganism of the species *Clostridium sporosphaeroides* is added. The pure culture is characterized biochemically by specific metabolic processes and activities, and by special growth conditions. Based on the specific metabolic processes and activities, the addition of a pure culture of a fermentative microorganism can make a special contribution to improved control of the complex biogas production process.

According to another preferred embodiment of the present invention, a microorganism of the species *Clostridium sporosphaeroides* is added as a constituent of at least one immobilized culture of microorganisms. As the amount of microorganisms isolated from their natural occurrence is not sufficient for the addition of microorganisms, usually multiplication is carried out in the form of a culture. It is found in practice that addition of the microorganisms to the fermentation substrate of a fermenter is carried out most simply in the form of an immobilized culture of microorganisms.

As the various beneficial effects on the fermentation process already mentioned are associated with the species of microorganism *Clostridium sporosphaeroides*, this species of microorganisms should be present in the added immobilized culture in an enriched amount compared with their natural occurrence. Of course, immobilized mixed cultures of any composition can be used for the addition. The only precondition is that microorganisms of the species *Clostridium sporosphaeroides* are contained in an amount that exceeds their natural occurrence.

According to preferred embodiments of the present invention, the microorganism of the species *Clostridium sporosphaeroides* accounts for at least $10^{-4}$% of the total number of microorganisms present in the immobilized culture added to the fermentation substrate. Especially preferably, the microorganism of the species *Clostridium sporosphaeroides* accounts for at least $10^{-2}$% of the total number of microorganisms present in the immobilized culture and especially preferably the microorganism of the species *Clostridium sporosphaeroides* accounts for at least 1% of the total number of microorganisms present in the immobilized culture.

According to further preferred embodiments, the microorganism of the species *Clostridium sporosphaeroides* accounts for at least 10% of the total number of microorganisms present in the immobilized culture, especially preferably the microorganism of the species *Clostridium sporosphaeroides* accounts for at least 50% of the total number of microorganisms present in the immobilized culture and especially preferably the microorganism of the species *Clostridium sporosphaeroides* accounts for at least 90% of the total number of microorganisms present in the immobilized culture.

According to a quite especially preferred embodiment, at least one immobilized pure culture of a microorganism of the species *Clostridium sporosphaeroides* is added.

Natural or synthetic polymers can be used as carrier materials, on which the microorganism *Clostridium sporosphaeroides* is immobilized. Gel-forming polymers are preferably used. These have the advantage that bacteria can be taken up or incorporated within the gel structure. It is preferable to use materials that are dissolved or degraded slowly in water, so that the release of the microorganism *Clostridium sporosphaeroides* proceeds over quite a long period.

Examples of suitable polymers are polyanillin, polypyrrole, polyvinylpyrolidone, polystyrene, polyvinyl chloride, polyvinyl alcohol, polyethylene, polypropylene, epoxy resins, polyethylene-imine, polysaccharides such as agarose, alginate or cellulose, ethylcellulose, methylcellulose, carboxymethyl ethylcellulose, cellulose acetates, alkali-cellulose sulfate, copolymers of polystyrene and maleic anhydride, copolymers of styrene and methylmethacrylate, polystyrene sulfonate, polyacrylates and polymethacrylates, polycarbonates, polyesters, silicones, cellulose phthalate, proteins such as gelatin, gum arabic, albumin or fibrinogen, mixtures of gelatin and waterglass, gelatin and polyphosphate, gelatin and copolymers of maleic anhydride and methylvinyl ether, cellulose acetate butyrate, chitosan, polydialkyldimethylammonium chloride, mixtures of polyacrylic acids and polydiallyldimethylammonium chloride and mixtures thereof. The polymer material can also be crosslinked by means of usual crosslinking agents such as glutaraldehyde, urea/formaldehyde resins or tannin compounds.

Alginates as immobilisates prove to be especially advantageous, because on the one hand they do not have a negative influence on the activity of the microorganism *Clostridium sporosphaeroides* and on the other hand they are degraded slowly by microorganisms. Through the slow degradation of the alginate immobilisates, the embedded microorganisms of the species *Clostridium sporosphaeroides* are released gradually.

For immobilization, the microorganisms are mixed with a polymer gel and then hardened in a suitable hardener solution. For this, they are first mixed with a gel solution and then added dropwise from a suitable height to a hardener solution. The precise procedures for immobilization are known by a person skilled in the art.

According to another preferred embodiment, at about the same time as the addition of the microorganisms described hereunder, additional biomass is added to the fermentation reactor. Addition of additional biomass "at about the same time" can take place within a time interval of from 1 second to up to 3 days after adding the microorganisms or it can take place simultaneously with the addition of the microorganisms. The volumetric loading in the fermentation reactor can then be increased continuously by continuous addition of new substrate or can be kept roughly constant, and fermentation can be carried out at all volumetric loadings, preferably at a volumetric loading of $\geq 0.5$ kg organic dry matter per m$^3$ per day [kgoDM/m$^3$d], more preferably at a volumetric loading of $\geq 4.0$ kgoDM/m$^3$d and especially preferably at a volumetric loading of $\geq 8.0$ kgoDM/m$^3$d, which compared with the present state of the art corresponds to more than doubling the volumetric loading.

The fermentation substrate used can in particular also have a high proportion of solid constituents. By adding a hydrolytically active, fermentative microorganism of the species *Clostridium sporosphaeroides*, these solid constituents are at least partially liquefied. The resultant liquefaction of the fermentation substrate through addition of the microorganism *Clostridium sporosphaeroides* can prevent and purposely counteract thickening of the fermenter material. Further feed of liquid to the fermentation substrate in the form of water or slurry during fermentation can be avoided. Thus, another advantage is saving of the resource fresh water. The resultant maintaining of stirrability and pumpability of the substrate is also advantageous. This means a saving on stirrers and pumps, and less energy is required for the stirring operation.

Microorganisms of the species *Clostridium sporosphaeroides* can thus also be used for the liquefaction of biomass in alcoholic fermentation for the purpose of production of biofuel.

According to another embodiment, treatment of the biomass takes place with constant thorough mixing of the fermentation substrate. With constant thorough mixing of the fermentation substrate, the cultures of *Clostridium sporosphaeroides* can be better distributed in the fermentation substrate. Moreover, in the case of biogas production, withdrawal of the resultant biogas from the fermentation process can be improved.

In addition, constant thorough mixing of the fermentation substrate leads to uniform heat distribution in the fermentation reactor. Measurements of the temperature in the fermentation reactor, which were carried out at regular intervals as well as continuously, showed that the fermentation substrate is fermented efficiently in a temperature range from 20° C. to 80° C., preferably at about 35° C. to 60° C., especially preferably at 40° C. to 50° C. These temperature ranges are therefore preferred within the scope of the present invention. In addition to hydrolysis, in particular the last stage of the fermentation process, namely the formation of methane by methanogenic microorganisms, takes place especially efficiently at higher temperatures. For multistage biogas installations it is also sensible to operate the different reactors at different temperatures, e.g. the first stage under mesophilic conditions and the subsequent stages, in particular methanogenesis, in thermophilic conditions. Suitable conditions for this are known from the prior art (e.g. DE 10 2005 012367 A1).

All embodiments of the present invention are not restricted to single-stage methods of production of biogas. Microorganisms of the species *Clostridium sporosphaeroides* can also be used in two-stage or multistage methods. Microorganisms of the species *Clostridium sporosphaeroides* can also be used in methods of production of liquid biofuels.

According to another embodiment, fermentation substrate and a microorganism of the species *Clostridium sporosphaeroides* are added continuously. Continuous operation of a fermentation reactor should, with a stable microbial biocoenosis, lead to continuous production of biogas, and exposure of the substrate addition to fermentation as a result of process disturbance should be reduced.

Carrying out of this method of fermentation and the associated processes in a discontinuous operation, for example "batch" fermentation, is also conceivable. Thus, according to another embodiment, the microorganism of the species *Clostridium sporosphaeroides* can be added to the fermentation substrate, for example at regular intervals during fermentation. Addition of the microorganism of the species *Clostridium sporosphaeroides* at regular intervals leads to an increase in the live cell count and therefore to an improved course of the fermentation processes, for example hydrolysis, with simultaneously improved utilization of the fermentation substrate for the fermentation.

According to a preferred embodiment of the present invention, the microorganism of the species *Clostridium sporosphaeroides* is added to the fermentation substrate in an amount such that after addition the proportion of the microorganism of the species *Clostridium sporosphaeroides* accounts for between $10^{-8}$% and 50% of the total number of microorganisms present in the fermentation substrate. In particular, depending on the size of the fermenter and therefore depending on the amount of fermentation substrate, addition of very widely varying amounts of microorganisms may be necessary for achieving the desired action.

Both determination of the total number of microorganisms in the fermentation substrate and determination of the proportions of different species of microorganisms in the fermentation substrate do not pose any problem for a person skilled in the art. For example, using fluorescence-labeled oligo-probes, the proportion of different microorganisms in the fermentation substrate can be identified specifically by the method described above.

Especially preferably, a microorganism of the species *Clostridium sporosphaeroides* is added to the fermentation substrate in an amount such that after addition the proportion of the microorganism of the species *Clostridium sporosphaeroides* accounts for between $10^{-6}$% and 25% of the total number of microorganisms present in the fermentation substrate. Especially preferably, the microorganism of the species *Clostridium sporosphaeroides* is added to the fermentation substrate in an amount such that, after addition, the proportion of the microorganism of the species *Clostridium sporosphaeroides* accounts for between $10^{-4}$% and 10% of the total number of microorganisms present in the fermentation substrate. Quite especially preferably, the microorganism of the species *Clostridium sporosphaeroides* is added to the fermentation substrate in an amount such that after addition the proportion of the microorganism of the species *Clostridium sporosphaeroides* accounts for between $10^{-3}$% and 1% of the total number of microorganisms present in the fermentation substrate.

Basically, the addition of microorganisms of the species *Clostridium sporosphaeroides* can take place at any time in the fermentation process, and in particular microorganisms of the species *Clostridium sporosphaeroides* can also be used for inoculation of fermentation substrate during initial start-up or restarting of a fermenter. Microorganisms of the species

*Clostridium sporosphaeroides* can be added in a suitable concentration and amount in the form of a culture once or several times at regular or irregular intervals, though preferably weekly or monthly, especially preferably daily or two to five times per week. Suitable concentrations of microorganisms and amounts added have already been stated or are described in the examples of application.

It is also possible to add microorganisms of the species *Clostridium sporosphaeroides* when there are disturbances of the fermentation process, for stabilization of fermentation. Such disturbances can be recognized early by monitoring certain characteristic parameters of fermentation. Characteristic parameters provide information on the quality of a fermentation process for the production of biogas while it is in progress. Said characteristic parameters are not only the amount of biogas produced and the methane content of the biogases produced, but for example also the hydrogen content of the biogases produced, the pH of the fermentation substrate, the redox potential of the fermentation substrate, the carboxylic acid content of the fermentation substrate, the proportions of various carboxylic acids in the fermentation substrate, the hydrogen content of the fermentation substrate, the proportion of dry matter in the fermentation substrate, the proportion of organic dry matter in the fermentation substrate, the viscosity of the fermentation substrate and the volumetric loading of the fermentation reactor.

The present invention also comprises the use of a microorganism of the species *Clostridium sporosphaeroides* for the treatment of biomass.

The present invention also comprises the use of a microorganism of the species *Clostridium sporosphaeroides* for the liquefaction of biomass.

The present invention also comprises the use of a microorganism of the species *Clostridium sporosphaeroides* for the production of biogas from biomass by fermentation.

The present invention also comprises the use of the liquefied biomass obtained by one of the methods described for the production of biofuel. The liquefied biomass obtained by one of the methods described is preferably used for the production of bioethanol.

The present invention also comprises the strain of the microorganism *Clostridium sporosphaeroides* SBG3, as was deposited under No. DSM 22577. The microorganism *Clostridium sporosphaeroides* SBG3 was deposited in a pure culture at the Deutsche Sammlung von Mikroorganismen und Zellkulturen GmbH in Brunswick according to the Budapest Treaty. The designation is: *Clostridium sporosphaeroides* SBG3 with the deposition number DSM 22577.

The present invention also comprises the strain of the microorganism *Clostridium sartagoformum* SBG1a, as was deposited under No. DSM 22578. The microorganism *Clostridium sartagoformum* SBG1a was deposited in a pure culture at the Deutsche Sammlung von Mikroorganismen und Zellkulturen GmbH in Brunswick according to the Budapest Treaty. The designation is: *Clostridium sartagoformum* SBG1a with the deposition number DSM 22578.

Bacteria of the species *Clostridium sporosphaeroides* can be isolated by methods known by a person skilled in the art from the fermentation substrate or fermentation residue of a fermenter. For this, a suitable substrate from a fermenter is transferred to a selection medium, cultivated for an extended period and finally individual colonies of microorganisms are isolated from the selection medium. After multiplication of the microbial DNA obtained therefrom by PCR, microorganisms of the species *Clostridium sporosphaeroides* can be selected on the basis of the DNA.

*Clostridium sporosphaeroides* SBG3 bacteria were isolated from the fermentation substrate of a postfermenter. For this, nitrogen and carbon dioxide were led through a liquid selection medium, then Na2S was added to the selection medium and autoclaved (20 min at 121° C.). Then the biomass obtained from the postfermenter was transferred to the selection medium and was cultivated for at least a week at a temperature of at least 30° C. A sample obtained from the liquid selection medium was transferred to a solid selection medium and then the colonies of microorganisms that grew on the solid selection medium were selected. After multiplying the microbial DNA obtained by PCR, comparison with known DNA sequences could be carried out.

After the *Clostridium sporosphaeroides* SBG3 bacteria had been isolated successfully from the fermentation substrate of the postfermenter, these microorganisms underwent sequence analysis. A partial sequence of 16S rRNA was determined, and was then transformed to the corresponding DNA sequence. The DNA sequence SEQ ID No. 1 comprises 1409 nucleotides. The microorganism *Clostridium* sp. clone 1099982248072 was identified as the nearest relative; this originated from a stool sample from a baby and so is not in any way connected with the industrial production of biofuels (GenBank identification number EF434352, length of sequence 1340 nucleotides). Sequence comparison showed that in the sequence of *Clostridium* sp. clone 1099982248072, compared with SEQ ID No. 1, altogether there were 46 nucleotide substitutions or gaps. For a length of sequence of *Clostridium* sp. clone 1099982248072 of 1340 nucleotides, identity is calculated as 96.57%.

The present invention also comprises microorganisms with a nucleic acid that has a nucleotide sequence that contains a sequence region that has more than 96.57% sequence identity with the nucleotide sequence SEQ ID No. 1. Especially preferably, the nucleotide sequence contains a sequence region that has more than 96.58% or more than 96.59% or more than 96.60% or more than 96.65% or more than 96.70% or more than 96.75% or more than 96.80% or more than 96.90% or more than 97.0% or more than 97.1% or more than 97.2% or more than 97.3% or more than 97.4% or more than 97.5% or more than 97.6% or more than 97.7% or more than 97.8% or more than 97.9% sequence identity with the nucleotide sequence SEQ ID No. 1.

Especially preferably, the nucleotide sequence contains a sequence region that has more than 98.0% sequence identity with the nucleotide sequence SEQ ID No. 1. Especially preferably, the nucleotide sequence contains a sequence region that has more than 98.1% or more than 98.2% or more than 98.3% or more than 98.4% or more than 98.5% or more than 98.6% or more than 98.7% or more than 98.8% or more than 98.9% sequence identity with the nucleotide sequence SEQ ID No. 1 and especially preferably the nucleotide sequence contains a sequence region that has more than 99% sequence identity with the nucleotide sequence SEQ ID No. 1.

According to further preferred embodiments, the microorganism has a nucleotide sequence that contains a sequence region that has more than 99.5% sequence identity with the nucleotide sequence SEQ ID No. 1 and especially preferably the nucleotide sequence contains a sequence region that has more than 99.8% sequence identity with the nucleotide sequence SEQ ID No. 1.

According to a quite especially preferred embodiment, the nucleotide sequence contains a sequence region that corresponds to the nucleotide sequence SEQ ID No. 1.

In preferred embodiments of the present invention there can be nucleotide mutations, relative to the initial nucleotide sequence SEQ ID No. 1, in one position or in two positions or in three positions or in four positions or in five positions or in six positions or in seven positions or in eight positions or in nine positions or in ten positions or in eleven positions or in twelve positions or in 13 positions or in 14 positions or in 15 positions or in 16 positions or in 17 positions or in 18 positions or in 19 positions or in 20 positions or in 21 positions or in 22 positions or in 23 positions or in 24 positions or in 25 positions or in 26 positions or in 27 positions or in 28 positions or in 29 positions or in 30 positions or in 31 positions or in 32 positions or in 33 positions or in 34 positions or in 35 positions or in 36 positions or in 37 positions or in 38 positions or in 39 positions or in 40 positions or in 41 positions or in 42 positions or in 43 positions or in 44 positions or in 45 positions or in 46 positions. The meaning of the term "nucleotide mutation" is explained in the "Definitions" section of the present text.

The present invention also comprises a culture of microorganisms suitable for use in a method of treatment of biomass, in particular a method of liquefaction of biomass and/or a method of production of biogas from biomass by fermentation, characterized in that a microorganism is present in the culture of microorganisms that has a nucleotide sequence that contains a sequence region that has at least 96.57% sequence identity with the nucleotide sequence SEQ ID No. 1, with the microorganism accounting for at least $10^{-4}$% of the total number of microorganisms present in the culture.

Preferably the culture of microorganisms suitable for use in a method of treatment of biomass, in particular a method of liquefaction of biomass and/or a method of production of biogas from biomass by fermentation contains a microorganism that has a nucleotide sequence with a sequence region that has more than 96.57% sequence identity with the nucleotide sequence SEQ ID No. 1. Especially preferably, the nucleotide sequence contains a sequence region that has more than 96.58% or more than 96.59% or more than 96.60% or more than 96.65 or more than 96.70 or more than 96.75 or more than 96.80% or more than 96.90% or more than 97.0% or more than 97.1% or more than 97.2% or more than 97.3% or more than 97.4% or more than 97.5% or more than 97.6% or more than 97.7% or more than 97.8% or more than 97.9% sequence identity with the nucleotide sequence SEQ ID No. 1.

Especially preferably, the culture of microorganisms suitable for use in a method of treatment of biomass, in particular a method of liquefaction of biomass and/or a method of production of biogas from biomass by fermentation, contains a microorganism that has a nucleotide sequence with a sequence region that has more than 98% sequence identity with the nucleotide sequence SEQ ID No. 1. Especially preferably, the nucleotide sequence contains a sequence region that has more than 98.1% or more than 98.2% or more than 98.3% or more than 98.4% or more than 98.5% or more than 98.6% or more than 98.7% or more than 98.8% or more than 98.9% sequence identity with the nucleotide sequence SEQ ID No. 1 and especially preferably, the nucleotide sequence contains a sequence region that has more than 99.0% sequence identity with the nucleotide sequence SEQ ID No. 1.

According to further preferred embodiments, the culture of microorganisms suitable for use in a method of treatment of biomass, in particular a method of liquefaction of biomass and/or a method of production of biogas from biomass by fermentation, contains a microorganism that has a nucleotide sequence with a sequence region that has more than 99.5% sequence identity with the nucleotide sequence SEQ ID No. 1. Quite especially preferably, the nucleotide sequence contains a sequence region that has more than 99.8% sequence identity with the nucleotide sequence SEQ ID No. 1.

According to a quite especially preferred embodiment, the culture of microorganisms suitable for use in a method of treatment of biomass, in particular a method of liquefaction of biomass and/or a method of production of biogas from biomass by fermentation contains a microorganism that has a nucleotide sequence that contains a sequence region that corresponds to the nucleotide sequence SEQ ID No. 1.

According to further preferred embodiments, the microorganism *Clostridium sporosphaeroides* accounts for at least $10^{-2}$%, preferably at least 1% of the total number of microorganisms present in the culture. Especially preferably, the microorganism *Clostridium sporosphaeroides* accounts for at least 10%, especially preferably at least 25% of the total number of microorganisms present in the culture.

Quite especially preferably, the microorganism *Clostridium sporosphaeroides* accounts for at least 50%, in particular at least 90% of the total number of microorganisms present in the culture. Especially preferably it is a pure culture of microorganisms suitable for use in a method of treatment of biomass, in particular a method of liquefaction of biomass and/or a method of production of biogas from biomass by fermentation, characterized in that it is a pure culture of the microorganism *Clostridium sporosphaeroides* SBG3 as was characterized above with respect to its nucleotide sequence.

Especially preferably, in the cases described above it is an immobilized culture of microorganisms.

The present invention also comprises an immobilized culture of microorganisms suitable for use in a method of treatment of biomass, in particular a method of liquefaction of biomass and/or a method of production of biogas from biomass by fermentation, characterized in that the immobilized culture of microorganisms contains a microorganism that has a nucleotide sequence that contains a sequence region that has at least 96.57% sequence identity with the nucleotide sequence SEQ ID No. 1.

Preferably, the immobilized culture of microorganisms suitable for use in a method of treatment of biomass, in particular a method of liquefaction of biomass and/or a method of production of biogas from biomass by fermentation, contains a microorganism that has a nucleotide sequence with a sequence region that has more than 96.57% sequence identity with the nucleotide sequence SEQ ID No. 1. Especially preferably, the nucleotide sequence contains a sequence region that has more than 96.58% or more than 96.59% or more than 96.60% or more than 96.65 or more than 96.70 or more than 96.75 or more than 96.80% or more than 96.90% or more than 97.0% or more than 97.1% or more than 97.2% or more than 97.3% or more than 97.4% or more than 97.5% or more than 97.6% or more than 97.7% or more than 97.8% or more than 97.9% or more than 98.0% or more than 98.1% or more than 98.2% or more than 98.3% or more than 98.4% or more than 98.5% or more than 98.6% or more than 98.7% or more than 98.8% or more than 98.9% sequence identity with the nucleotide sequence SEQ ID No. 1. Especially preferably, the nucleotide sequence contains a sequence region that has more than 99.0% sequence identity with the nucleotide sequence SEQ ID No. 1.

According to further preferred embodiments, the immobilized culture of microorganisms suitable for use in a method of treatment of biomass, in particular a method of liquefaction of biomass and/or a method of production of biogas from biomass by fermentation, contains a microorganism that has a nucleotide sequence that has a sequence region that has more than 99.5% sequence identity with the nucleotide sequence SEQ ID No. 1. Quite especially preferably, the nucleotide sequence contains a sequence region that has more than 99.8% sequence identity with the nucleotide sequence SEQ ID No. 1.

According to a quite especially preferred embodiment, the immobilized culture of microorganisms suitable for use in a method of treatment of biomass, in particular a method of liquefaction of biomass and/or a method of production of biogas from biomass by fermentation, contains a microorganism that has a nucleotide sequence that contains a sequence region that corresponds to the nucleotide sequence SEQ ID No. 1.

In addition, the present invention comprises the use of microorganisms as were characterized above with respect to their nucleotide sequence in a method of treatment of biomass. Preferably, these microorganisms are used in one of the methods of treatment of biomass explained in more detail above.

The present invention further comprises the use of microorganisms as were characterized above with respect to their nucleotide sequence in a method of liquefaction of biomass. Preferably, these microorganisms are used in one of the methods of liquefaction of biomass explained in more detail above.

The present invention further comprises the use of microorganisms as were characterized above with respect to their nucleotide sequence in a method of production of biogas from biomass by fermentation. Preferably, these microorganisms are used in one of the methods explained in more detail above for the production of biogas from biomass by fermentation.

The present invention further comprises the use of a culture of microorganisms as were characterized above with respect to their nucleotide sequence in a method of treatment of biomass. Preferably, these cultures of microorganisms are used in one of the methods of treatment of biomass explained in more detail above.

The present invention further comprises the use of a culture of microorganisms as were characterized above with respect to their nucleotide sequence in a method of liquefaction of biomass. Preferably, these cultures of microorganisms are used in one of the methods of liquefaction of biomass explained in more detail above.

The present invention further comprises the use of a culture of microorganisms as were characterized above with respect to their nucleotide sequence in a method of production of biogas from biomass by fermentation. Preferably, these cultures of microorganisms are used in one of the methods of production of biogas from biomass by fermentation explained in more detail above.

BRIEF DESCRIPTION OF THE DRAWINGS

To illustrate the invention and clarify its advantages, examples of application are given below. The examples of application will be explained in more detail with reference to FIGS. 1 to 4. It goes without saying that the statements made in connection with the examples of application are not intended to limit the invention. The figures show.

WAYS OF CARRYING OUT THE INVENTION

Figure 1:
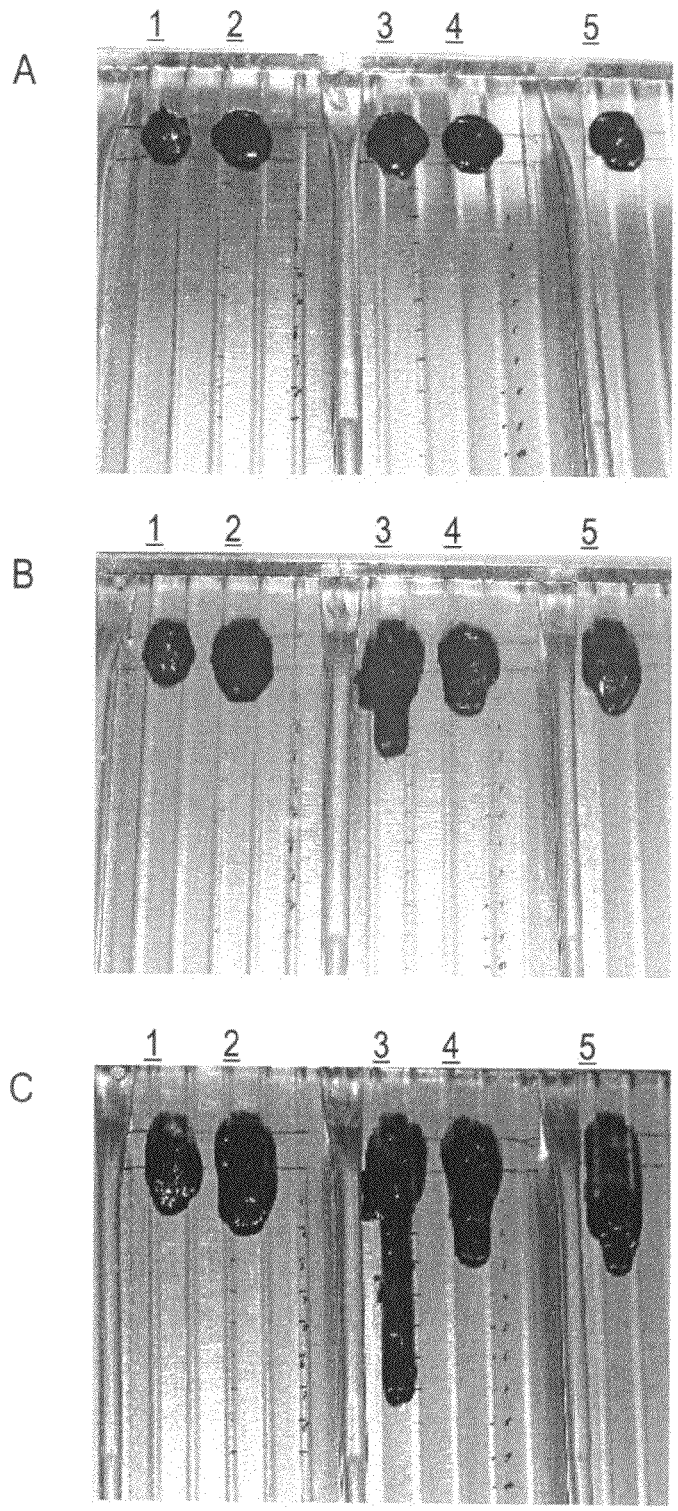
FIG. 1 A substrate flow test for investigating the extent of liquefaction of the fermentation substrate.

*Clostridium sporosphaeroides* SBG3 bacteria were successfully isolated from the fermentation substrate of a postfermenter. The organism was deposited in a pure culture at the Deutsche Sammlung von Mikroorganismen und Zellkulturen GmbH (DSMZ) according to the Budapest Treaty (*Clostridium sporosphaeroides* SBG3 with the deposition number DSM 22577).

*Clostridium sartagoformum* SBG1a bacteria were also successfully isolated from the fermentation substrate of a postfermenter. The organism was deposited in a pure culture at the Deutsche Sammlung von Mikroorganismen und Zellkulturen GmbH (DSMZ), *Inhoffenstr, 7B*, Braunschweig, Germany D-38124 on May 15, 2009, according to the Budapest Treaty (*Clostridium sartagformum* SBG1a with the deposition number DSM 22578).

As can be seen from the following examples of application, bacteria of the strain *Clostridium sartagoformum* SBG1a, both in mixed culture and in pure culture according to the invention, have properties similar to those of bacteria of the strain *Clostridium sporosphaeroides* SBG3, e.g. an increase in volumetric loading, an increase in gas yield and stabilization of the biogas process, and capacity for liquefaction of biomass.

Unless stated otherwise below, standard biomolecular methods were used, for example as described by Sambrook et al., 1989, Molecular cloning: A laboratory manual 2nd edition, Cold Spring Harbor Laboratory Press, Cold Spring Harbor, N.Y.

Isolation and Enrichment of the Microorganisms

Bacteria of the strain *Clostridium sporosphaeroides* SBG3 were successfully isolated from the fermentation substrate of a postfermenter. The microorganisms were isolated using a selection medium that contained carboxymethylcellulose (CMC) as the only source of carbon. Carboxymethylcellulose is very similar to the cellulose contained in fermentation substrates of biogas installations and moreover has improved solubility in aqueous medium through the linking of the hydroxyl groups with carboxymethyl groups (—$CH_2$—COOH—). The medium used for selection of *Clostridium sporosphaeroides* SBG3 (DSMZ Medium 520 plus 1% CMC and 0.2% yeast extract) was gassed with N2, so that selection could take place under anaerobic conditions. The residual oxygen it contained was reduced with 0.5 g/l Na2S.

The selection medium was then inoculated with the supernatant from material from a postfermenter (diluted 1:2000). After cultivation for 1 week at 40° C., microscopic analysis detected individual rods. Further selection of the liquid cultures and isolation as far as pure cultures were carried out by streaking on anaerobic carboxymethylcellulose plates.

For larger amounts of bacteria of the strain *Clostridium sporosphaeroides* SBG3 (e.g. for addition to fermenter type 3) they were grown in the stated conditions in a 1 m³ fermenter, which was inoculated with 100 ml of preculture. As growth is very rapid, with a doubling time of about 2 h, *Clostridium sporosphaeroides* SBG3 appears to be especially suitable for biotechnological use. Smaller amounts of bacteria (e.g. for addition to fermenter types 1, 2 and 4) were cultivated at the 500 ml to 1 l scale. Cultivation for addition to a fermentation process took place over a period of 1 to 2 days. Cell densities in the range from 108 to 1010 cells per ml culture medium were reached. The bacterial cells were harvested by centrifugation and taken up in the smallest possible volume of fresh medium before they were used in the fermentation process. For interim storage the cells were frozen.

Microorganisms of the species *Clostridium sartagoformum* and *Paenibacillus macerans*, e.g. for the use of mixed cultures with roughly equal proportions of the 3 microorganisms mentioned, were cultivated under the same conditions.

DNA Isolation and Determination of Nucleotide Sequences

The cellular material of the grown isolated colonies was used for multiplying the microbial DNA by the Colony-PCR method according to a standard program.

For determination of the 16S rRNA sequence, the gene for the 16S rRNA was amplified from the cell DNA by PCR. The primers with the sequences GRGTTTGATCCTGGCTCAG and ACGGHTACCTTGTTACGACTT were used for this (stated in 5→3' direction; H denotes C, T or A). The pieces of DNA obtained as PCR products were then cloned into a cloning vector (ligation with the QIAGEN PCR Cloning Kit from the company QIAGEN/Hilden using the p-Drive vector), transformed in *E. coli* (according to QIAGEN PCR Cloning Handbook) and investigated by Colony-PCR. The Colony-PCR products obtained underwent restriction fragment length polymorphism analysis (RFLP) for selecting suitable clones. The corresponding plasmid-DNA was isolated from the respective clones and was sequenced by the chain terminating technique (Sanger et al., 1977).

Sequence Analysis

After sequence analysis of the colonies, the 16S rDNA or its transformation into the corresponding 16S rRNA was analyzed phylogenetically with the software package ARB (Ludwig et al., Nucleic Acids Research. 2004. 32, 1363-1371) and was classified as a microorganism of the species *Clostridium sporosphaeroides*. Based on an analysis of the cloned 16S rDNA or of the corresponding 16S rRNA sequence using the BLAST program (basic local alignment search tool) from the database www.ncbi.nlm.nih.gov, the *Clostridium* sp. clone 1099982248072 was determined as the nearest relative.

Liquefaction of Cellulose-Containing Medium

Tests with a pure culture of the hydrolytically active, fermentative microorganism *Clostridium sporosphaeroides* SBG3 showed that addition to the highly viscous carboxymethylcellulose-containing selection medium leads to successive liquefaction of the medium until it is of a watery consistency during bacterial growth, which can be clearly observed by shaking the culture flask and visual inspection.

Liquefaction of Fermentation Substrate—Substrate Flow Test

Liquefaction of a fermentation substrate with high dry matter content or maintaining a liquid-slurry consistency in a wet fermentation process is essential to ensure a smooth and cost-effective course of the technical process. Sometimes in continuous operation there is also increasing "gelification" of the fermenter contents, which also has an adverse effect on the process of biogas production. The effect that the addition of microorganisms had on the consistency of the fermentation substrate was determined with a test that measured the flow behavior of substrate samples on an inclined plane (substrate flow test).

The starting material for the flow test was material from a biogas plant with a proportion of dry matter of approx. 8-12%. In each case 500 ml of material from a fermenter was poured into 1 l Schott bottles and incubated for 1 day at 40° C. Then in each case the bacterial cell mass from 500 ml of preculture (equivalent to about 4×10¹¹ cells) of *Clostridium sporosphaeroides* SBG3, *Clostridium sartagoformum* SBG1a, *Paenibacillus macerans* SBG2 or a mixture of the three bacteria in equal proportions was resuspended in 1 ml of medium, added and incubated for a further 5 days at 40° C. with shaking. For the control sample, only 1 ml of medium was added. In each case 1.3 g of the samples was put on the starting point of the inclined plane made of metal and the flow rate (distance covered per 10 min) of the respective samples was read from a cm-scale, and represents a measure for the liquefaction or the viscosity of the fermentation substrate. The results of the flow test are shown in FIG. 1.

FIG. 1 shows the following tracks: track 1: control without addition of microorganisms (comparative example); track 2: *Clostridium sartagoformum* SBG1a (comparative example); track 3: *Clostridium sporosphaeroides* SBG3; track 4: *Paenibacillus macerans* SBG2 (comparative example); track 5: mixture of *Clostridium sartagoformum* SBG1a, *Clostridium sporosphaeroides* SBG3 and *Paenibacillus macerans* SBG2 in equal parts. FIG. 1A shows the tracks directly after applying the samples, FIG. 1B after 2 min and FIG. 1C after 18 min.

It was found that the viscosity of the fermenter contents decreased very markedly as a result of adding live bacteria of the strain *Clostridium sporosphaeroides* SBG3, whereas addition of the organisms *Clostridium sartagoformum* SBG1a and *Paenibacillus macerans* SBG2 also had a clear, but less pronounced effect. A significant liquefaction of the substrate was also achieved on adding the mixture of the 3 microorganisms. It was shown in another test that the addition of dead cells (dead-autoclaved) had practically no effect. Visual inspection of the samples also showed that on adding living cells of the strain *Clostridium sporosphaeroides* SBG3 the proportion of mucilaginous substances decreased. It was surprising that the added bacteria also brought about further liquefaction of a substrate that had already passed through a fermenter and therefore fermentation process by microorganisms. This means that in a fermentation process without external addition of microorganisms, the substrate is not degraded completely, but has additional energy potential, which can be utilized by adding the microorganisms according to the invention.

Determination of Cell Density

To determine the cell density with respect to live bacteria, in each case 10 μl of bacterial sample (e.g. preculture, bacterial culture feed, supernatant from fermenter sample) was mixed with 2 μl BacLight™ dye (Invitrogen) and examined under the microscope at 1000× magnification (AXIO Imager A1, Zeiss, Jena). Under UV light and using two different filters, with the BacLight™ system it is possible to determine the proportion of live cells in the sample. The total cell count was counted in a Thoma counting chamber. The proportion of live cells from the precultures was as a rule higher than 90%.

Determination of the Proportion of Cells of *Clostridium Sporosphaeroides* SBG3 or *Paenibacillus Macerans* SBG2 or *Clostridium Sartagoformum* SBG1a in a "Fishing" Sample The proportion of bacteria of the species *Clostridium sporosphaeroides* SBG3 or *Paenibacillus macerans* SBG2 or *Clostridium sartagoformum* SBG1a was determined by "whole cell hybridization" according to the method described in Amann et al. (1995, Microbiol. Rev. 59, 143-169). The probe used for "Fishing" was a labeled oligonucleotide with the sequence Cy3-ccacagctctcacgcccg (given in 5'→3' direction) for *Clostridium sporosphaeroides* SBG3, a labeled oligonucleotide with the sequence Cy3-gcaacccgaacTgagacc (given in 5→'3' direction) for *Paenibacillus macerans* SBG2 and a labeled oligonucleotide with the sequence Cy3-CT-TCATGCGAAAATGTAA (given in 5'→3' direction) for *Clostridium sartagoformum* SBG1a. The oligonucleotides had as marker, in each case on the 5'-end, the dye indocarbocyanin (Cy3).

Fermenter Types

Tests were conducted at the pilot plant scale in various fermenter types. The fermenters were operated at operating temperatures of approx. 40° C. The substrate used was mainly maize silage with a proportion of organic dry matter (oDM) of 30-35%. To ensure supply of trace elements for the metabolically active microorganisms involved in fermentation, as a rule commercially available mixtures of trace elements were added (e.g. Novodyn®).

Fermenter type 1: Horizontal plug-flow fermenter, rectangular, volume 150 l, designed with subdivision of the fermenter space by integral wall with small-area opening for the substrate stream, division of the fermenter space in ¼ directly after substrate feed nozzles and ¾ after apertured diaphragm, 2-stage plant.

Fermenter type 2: Horizontal plug-flow fermenter, rectangular, volume 150 l as 1st stage plus fully mixed round fermenter, volume 200 l as 2nd stage; total volume 350 l. 2-stage plant with recirculation between round fermenter and plug-flow fermenter.

Fermenter type 3: Horizontal plug-flow fermenter, cylindrical, volume 30 $m^3$, 1-stage plant.

Fermenter type 4: Horizontal plug-flow fermenter, rectangular, volume 150 l, no designed subdivision in the fermenter space, 1-stage plant. Optional recirculation.

Distribution of Microorganisms Within the Fermenter—"Tracer Rest"

As the thorough mixing of the tough substrate and therefore also other additives in a fermenter takes some time and depends moreover on the stirring technology used, a test was established for determining the length of time to uniform distribution of added microorganisms in the fermenter. In this "tracer test", instead of microorganisms, powdered LiCl was added at a concentration of 10 mg lithium/kg of starting substrate (twice this amount for fermenter type 2) at the place of substrate addition. Then after various times (addition takes place on day 1), substrate samples are taken at various points of the fermenter (at the start of the fermenter after substrate feed and at the end before discharge of the residual substrate) and these are analyzed for their Li content by inductively coupled plasma-atom-emission spectroscopy according to the methods of DIN EN ISO 13346 (S7a) and DIN EN ISO 11885 (E22). After complete thorough mixing of the fermenter contents, the measured Li content at the front end of the fermenter and at the rear end of the fermenter should be equal and have a value of approx. 10 mg/kg of starting substrate (approx. 20 mg/kg of starting substrate for fermenter type 2). The results of these "tracer tests" for 3 different fermenter types are shown in Table 1.

TABLE 1

| Day | Fermenter type 1 Lithium [mg/kg of starting substrate] | | Fermenter type 2 Lithium [mg/kg of starting substrate] | | Fermenter type 3 Lithium [mg/kg of starting substrate] | |
|---|---|---|---|---|---|---|
| | front | rear | front | rear | front | rear |
| 1 | 1.7 | 1.0 | 9.0 | 9.8 | 4.5 | 3.8 |
| 2 | 23.6 | 5.9 | 25.0 | 16.6 | | |
| 3 | 18.5 | 8.8 | 26.8 | 19.6 | 15.2 | 5.1 |
| 4 | 14.7 | 10.6 | 25.3 | 21.4 | | |
| 5 | | | 21.3 | 22.2 | 11.9 | 11.0 |
| 7 | | | | | 10.7 | 11.6 |
| 8 | 11.1 | 11.8 | 18.0 | 20.3 | 12.0 | 11.7 |
| 10 | | | | | 10.7 | 12.0 |
| 11 | | | 19.1 | 19.0 | | |

It was observed that complete thorough mixing of the fermenter contents and accordingly uniform distribution of the "tracer" for fermenter types 2 and 3 was attained five days after adding the "tracer", but in fermenter type 1 only after 8 days. It is to be assumed that the time taken for uniform distribution of added microorganisms is also several days.

Long-Term Fermentation for Biogas Production with or without Addition of Microorganisms According to the Invention At the pilot-plant scale, at least doubling of the average volumetric loading known from practice could regularly be achieved. Stable operation was achieved at a volumetric loading of 8 kgoDM/$m^3$d by adding 2×$10^{13}$ cells per $m^3$ per week. No changes were made to the process parameters usually employed in practice, such as temperature (40° C.) and pH (6-9), or buffer capacity.

During the fermentation process in various experimental fermenters with a volume of 150 l to 30000 l under realistic plant operating conditions (T~40° C., pH 6-8, continuous charging, constant thorough mixing), the variation of the volumetric loading of the fermenter in kilograms of organic dry matter per cubic meter per day (kgoDM/$m^3$d) as a function of time, and the variation of biogases produced as a function of time, were determined over a period of several months. For better comparability of the various experimental installations, instead of using the specific biogas yield, the gas yield was given as the space-time yield (standard liters of biogas produced per liter of fermentation volume, [Nl/l]), for which the amount of biogas produced was standardized to the particular fermentation volume. The variation of the theoretically expected gas output as a function of time was also calculated.

The Kuratorium für Technik and Bauwesen in der Landwirtschaft e.V. (KTBL; "The Association for Technology and Structures in Agriculture"), as well as the Federal Research Institute for Agriculture and the Agency for Renewable Resources, have published guidelines for the approximate amounts of biogas that are to be expected in stable fermentation, depending on the substrate used. These theoretical guide values can therefore reflect the amount of biogas that can theoretically be produced. Alternatively, guide values published by other institutes in other countries can also be used. For maize silage, for which the proportions of oDM were between 22% and 40%, expected gas outputs were stated to be in the region of 533 Nl/kgoDM and 650 Nl/kgoDM (in "Handreichung Biogasgewinnung and -nutzung" (Recommendations on biogas production and utilization), 2006, Publ. Fachagentur Nachwachsende Rohstoffe e.V., Gülzow and KTBL Homepage, www.ktbl.de). The variation of theoretical gas production as a function of time [Nl/d] was calculated according to these guide values, assuming in all tests the very high value for theoretical gas output of 663 Nl/kgoDM. The actual measured values for the proportions of oDM in the maize silage used fluctuated between 30 and 40% oDM depending on the charge.

Apart from gas yield and volumetric loading, a number of other characteristic parameters of the fermentation process were measured, such as dry matter content of the fermenter contents, pH, concentration of acids (e.g. acetic acid, propionic acid, butyric acid, valeric acid, acetic acid equivalent), temperature, specific gas yield, composition of the biogas, viscosity, conductivity, redox potential and the concentration of nutrients and trace elements.

Long-Term Fermentation in a Fermenter of Type 4 with Addition of Microorganisms *Clostridium Sporosphaeroides* SBG3

The pilot plant is a horizontal, rectangular plug-flow fermenter with a volume of 150 l. The fermenter was operated as a 1-stage plant.

Figure 2:
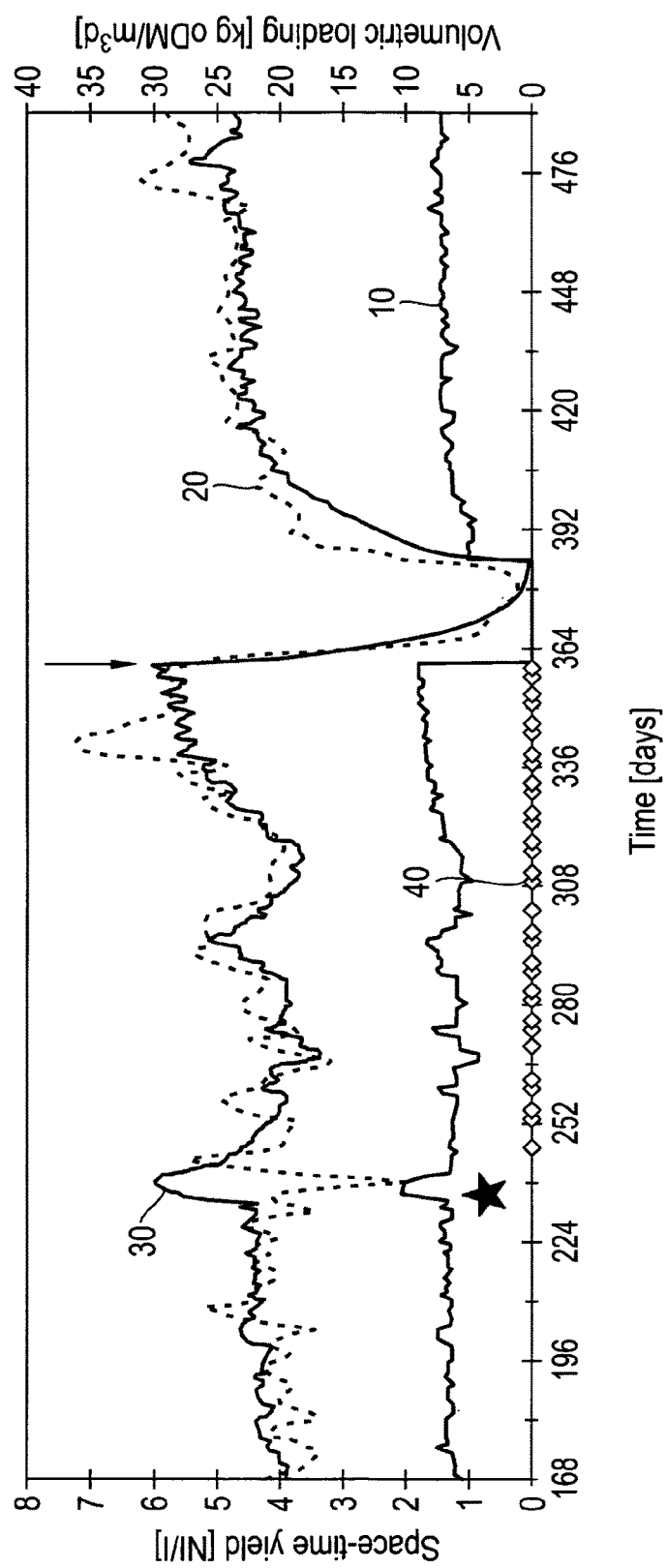
FIG. 2 Measured results from fermentation: the gas output as space-time yield (NI/I) and the volumetric loading of the fermenter are plotted as a function of time.

FIG. 2 shows measured results for various characteristic parameters during a fermentation process in an experimental fermenter with and without addition of microorganisms of the strain *Clostridium sporosphaeroides* SBG3. The curve with the reference symbol 10 shows the variation of the volumetric loading of the fermenter as a function of time in kilograms of organic dry matter per cubic meter per day (kgoDM/m$^3$d) and the curve with the reference symbol 20 shows the variation of the measured space-time yield as a function of time, in each case averaged over 5 days (Nl/l). The reference symbol 30 is used for the variation of the theoretical gas production as a function of time, in [Nl/l].

Up to operating day 246, the plant was operated without addition of microorganisms. In this plant, a very high volumetric loading between 6 and 7 kgoDM/m$^3$d was achieved in stable fermentation, but in each case the actual gas yield remained somewhat below the theoretical.

Starting from day 232 (star symbol), increasing the volumetric loading to 10 kgoDM/m$^3$d was tried, but this led to immediate collapse of biogas production. After the volumetric loading had been brought back to a value of approx. 6 kgoDM/m$^3$d, starting from day 246, cultures of microorganisms of the strain *Clostridium sporosphaeroides* SBG3 were added twice per week (between 5×10$^{10}$ and 2×10$^{11}$ cells per addition in a volume of 30 to 200 ml). The timepoints for addition of *Clostridium sporosphaeroides* SBG3 are indicated by diamond symbols 40 on the X-axis.

After that, the actual gas yield was permanently above the theoretically calculated value. The volumetric loading could be increased continuously in a stable fermentation process and by day 360 had been increased to a value of 9 kgoDM/m$^3$d. Therefore the space-time yield also rose from the initial 4 Nl/l to 6 Nl/l. After day 360 (arrow), owing to a pause in operation, substrate feed was stopped and no further additions of microorganisms were made. Gas production came to a complete standstill.

Starting from day 384, the plant was returned within a day to a volumetric loading of 5 kgoDM/m$^3$d without adding microorganisms again. Up to about day 415 the volumetric loading had been increased to a value of 7 kgoDM/m$^3$d and thereafter always remained at high values between 7 and 8 kgoDM/m$^3$d. Gas production became highly efficient again and remained in the region of or above the theoretically expected gas production for the entire observation period.

A person skilled in the art will be aware that problem-free start-up of a plant in this way after shutdown for several weeks is very unusual. "Fishing" experiments, after the plant had been restarted, with an oligonucleotide probe against *Clostridium sporosphaeroides* SBG3 showed that the organism had become established in the fermenter and was present at a concentration of about 0.5% of the total number of bacteria detectable in the fermenter contents. This also explains the beneficial effects of increased volumetric loading and gas yield and the stability of the fermentation process, which had already been observed previously with regular addition of the microorganism *Clostridium sporosphaeroides* SBG3.

Long-Term Fermentation in a Fermenter of Type 1 with Addition of Microorganisms *Clostridium Sporosphaeroides* SBG3 and a Mixture of Microorganisms of the Strains *Clostridium Sporosphaeroides* SBG3, *Clostridium Sartagoformum* SBG1a and *Paenibacillus Macerans* SBG2

The pilot plant is a horizontal, rectangular plug-flow fermenter with a volume of 150 l. The fermenter was operated as a 2-stage plant, as it was designed with subdivision of the fermenter space by an integral wall with a small-area opening for the substrate stream. The fermenter space could be regarded as being divided into 2 reaction spaces, in the volume ratio 1:3, the space directly after the substrate feed nozzles being the smaller, and the space after the apertured diaphragm being the larger. Measurements of characteristic fermentation parameters showed that sometimes different values were obtained in the two reaction spaces, so that it can be assumed that different substrate reactions also took place preferentially in one or other reactor space.

Figure 3:
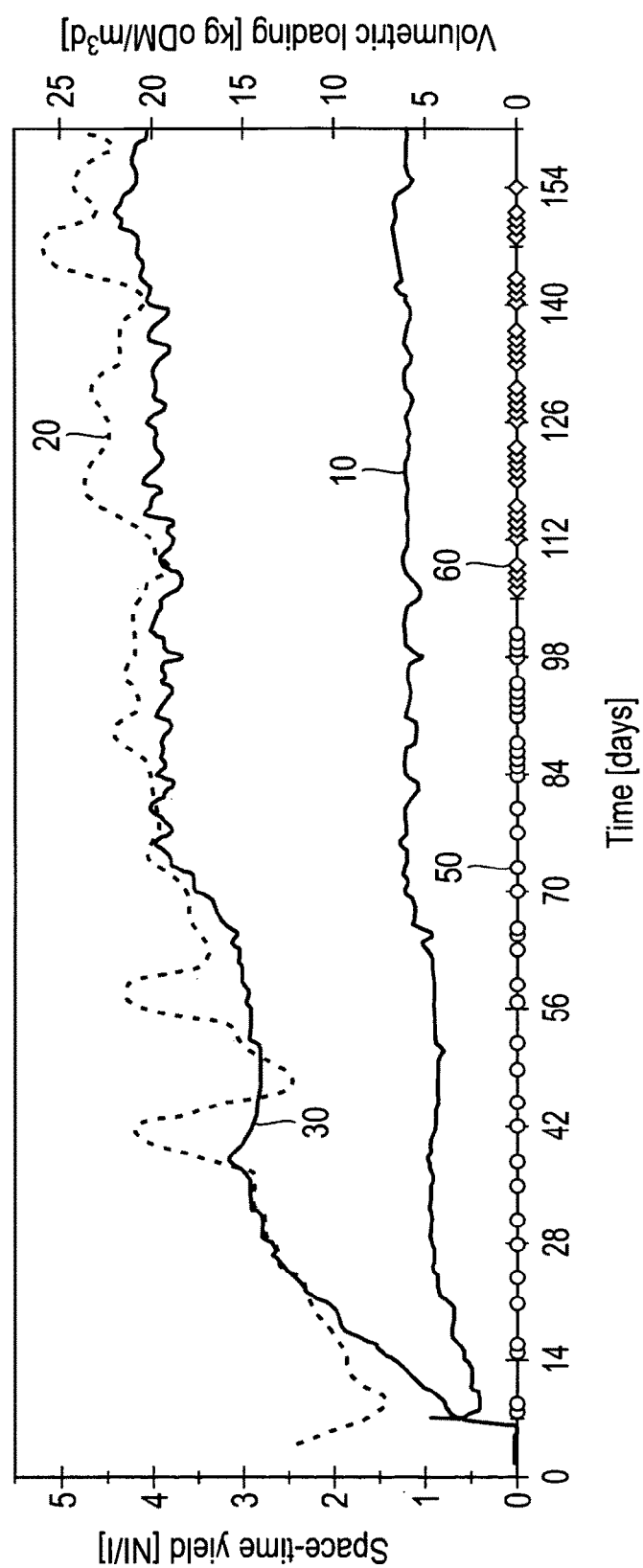
FIG. 3 Measured results from another fermentation: the gas output as space-time yield (NI/I) and the volumetric loading of the fermenter are plotted as a function of time.

FIG. 3 shows measured results for various characteristic parameters during a fermentation process in an experimental fermenter of type 1 with addition of a mixture of microorganisms or of microorganisms of the strain *Clostridium sporosphaeroides* SBG3. The curve with the reference symbol 10 shows the variation of the volumetric loading of the fermenter as a function of time in kilograms of organic dry matter per cubic meter per day (kg oDM/m$^3$d) and the curve with the reference symbol 20 shows the variation of the measured space-time yield as a function of time, in each case averaged over 5 days (Nl/l). Reference symbol 30 indicates the variation of theoretical gas production as a function of time in [Nl/l].

The plant received a completely fresh charge. After just one week, a mixed culture of roughly equal proportions of microorganisms of the strains *Clostridium sporosphaeroides* SBG3, *Clostridium sartagoformum* SBG1a and *Paenibacillus macerans* SBG2 was added 2 to 5 times per week. The timepoints of the additions are indicated with the reference symbol 50. In each case approx. 3 g cell pellets with a cell count of about 10$^{12}$ cells were added. In a stable fermentation process, the volumetric loading could be increased gradually to a value of approx. 6 kgoDM/m$^3$d. The gas output achieved corresponded as a rule to the theoretically expected value or was slightly lower.

Starting from day 106, instead of the mixed culture, only a pure culture of the strain *Clostridium sporosphaeroides* SBG3 was added 5 times per week (also approx. 3 g cell pellets with a cell count of about 10$^{12}$ cells). The timepoints of the additions are indicated with the reference symbol 60. The volumetric loading was maintained at a constant high level of 6 and 7 kgoDM/m$^3$d up to the end of the observation period, without the measured acid concentrations entering critical ranges. The measured proportions for the organic dry matter in the fermenter contents never exceeded a value of 12% oDM, so that even at high volumetric loading there was an easily stirred, not too viscous mass in the fermenter. In control experiments without addition of microorganisms, this type of fermenter could never be operated with a volumetric loading of more than 5 kgoDM/m$^3$d.

On adding a pure culture of the strain *Clostridium sporosphaeroides* SBG3, the actual measured gas yield increased significantly compared with the period during which the mixed culture was added. For the period in which the mixed culture was added 5 times per week, an average gas output of 4.1 Nl/l was measured, whereas after addition of the pure culture of *Clostridium sporosphaeroides* SBG3 an average gas output of 4.6 Nl/l was determined, which corresponds to a 12% increase and is economically significant. This example also shows that when a pure culture of the strain *Clostridium sporosphaeroides* SBG3 was added, the specific biogas yield (Nm3/t) rose, since the gas yield increased at constant volumetric loading, and accordingly the added substrate was utilized more efficiently.

Long-Term Fermentation in a Fermenter of Type 3 with Addition of Microorganisms *Clostridium Sporosphaeroides* SBG3

This experimental plant is a large test plant at the pilot-plant scale with a volume of 30 m$^3$, constructed as a horizontal, cylindrically shaped plug-flow fermenter. It is operated as a 1-stage plant.

Figure 4:
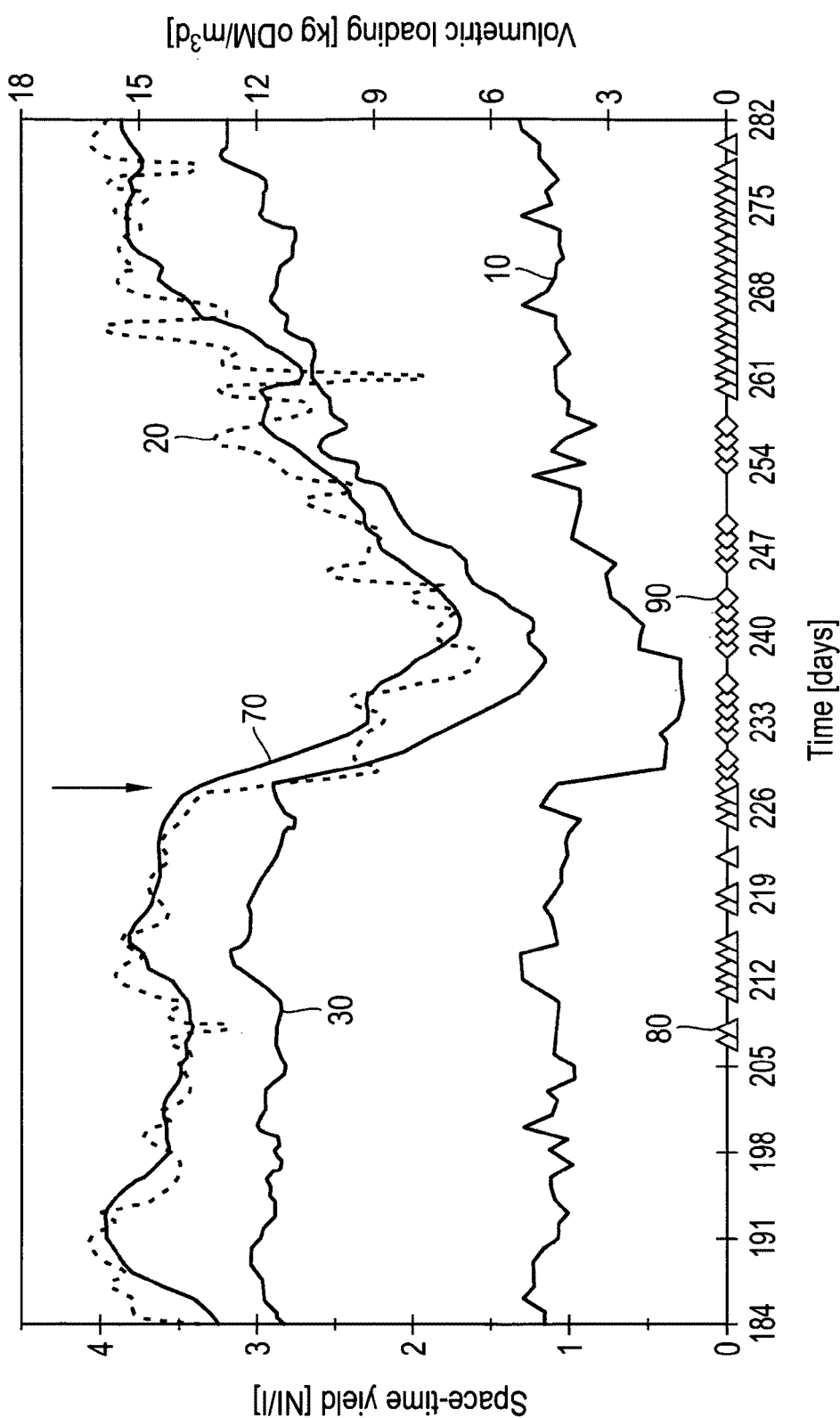
FIG. 4 Measured results from another fermentation: the gas output as space-time yield (NI/I) and the volumetric loading of the fermenter are plotted as a function of time.

FIG. 4 shows measured results for various characteristic parameters during a fermentation process in an experimental fermenter of type 3 with addition of microorganisms of the strain *Clostridium sartagoformum* SBG1a or of microorganisms of the strain *Clostridium sporosphaeroides* SBG3. The curve with the reference symbol 10 shows the variation of the volumetric loading of the fermenter as a function of time in kilograms of organic dry matter per cubic meter per day (kgoDM/m$^3$d) and the curve with the reference symbol 20 shows the variation of the measured space-time yield as a function of time. The space-time yield, in each case averaged over 5 days (Nl/l), is indicated with the reference symbol 70. Reference symbol 30 indicates the variation of the theoretical gas production as a function of time in [Nl/l].

The timepoints of the additions of microorganisms of the strain *Clostridium sporosphaeroides* SBG3 are indicated with the reference symbol 90. The timepoints of the additions of microorganisms of the strain *Clostridium sartagoformum* SBG1a are indicated with the reference symbol 80. The arrow marks the start of the "crash" of the fermenter.

Starting from operating day 184, the biogas plant was operated with a volumetric loading in the range from 4 to 5 kgoDM/m$^3$d. As can be seen from FIG. 4, the space-time yield of biogas achieved in this test is well above the theoretically expected value. In order to keep the process at this high level, starting from day 207, pure cultures of microorganisms of the strain *Clostridium sartagoformum* SBG1a were added (4 to 5 times per week in each case approx. 100 g of moist cell pellets from a 100 to 200 l batch, corresponds to approx. 4 to 8 times 1013 cells). In this way, the process could be maintained at this high level (space-time yield in the range 3.5 to 4 Nl/l, approx. 15% to 30% above the theoretically expected gas output) for more than 2 weeks. Starting from day 227, however, there was a sudden drop in gas formation accompanied by a rapid decline of the volumetric loading to a value of just a little above 1 kgoDM/m$^3$d, which amounts to a "fermenter crash". That the fermentation process had departed from equilibrium could also be seen from other measured process variables such as pH (drop in pH from approx. 7.7-7.8 to a value of 6.0 on day 229) and the measured values for accumulation of free fatty acids (dramatic increase in the values for acetic acid, propionic acid, butyric acid, valeric acid and acetic acid equivalent). In order to stabilize the fermentation process again, on and after operating day 228, in each case a pure culture of microorganisms of the strain *Clostridium sporosphaeroides* SBG3 was added (4 to 5 times per week, approx. 100 g moist cell pellets from a 100 to 200 l batch). During the crash, the gas yield achieved still reached the theoretically expected value (see measurement series with the reference symbols 20 and 30), but already starting from day 230, i.e. 2 days after adding the first culture of microorganisms of the strain *Clostridium sporosphaeroides* SBG3, the measured gas outputs are once again above the theoretically expected values. Increase in volumetric loading accompanied by continuously increasing gas outputs was possible starting from day 238. Addition of microorganisms of the strain *Clostridium sporosphaeroides* SBG3 was continued up to day 257. At this timepoint a volumetric loading of approx. 4 kgoDM/m$^3$d was reached, and the gas yield achieved was always far above the theoretically calculated value, but the efficiency level was still somewhat lower than before the crash. Addition of microorganisms of the strain *Clostridium sporosphaeroides* SBG3 was then stopped and, starting from day 260, microorganisms of the strain *Clostridium sartagoformum* SBG1a were added again (4 to 5 times per week in each case approx. 100 g moist cell pellets from a 100 to 200 l batch). It was found that as a result the space yield could again be increased slightly to values between 4.5 and 5 kgoDM/m$^3$d and an increased gas output was observed again, reaching the level before the fermenter crash. The addition of microorganisms of the strain *Clostridium sporosphaeroides* SBG3 according to the invention proved suitable for stabilizing a fermenter during a crash, so that efficient biogas production could be resumed.

By adding pure cultures of *Clostridium sporosphaeroides* SBG3, the volumetric loading during fermentation could be increased to a maximum value of about 9 kgoDM/m$^3$d.

In parallel with the increasing volumetric loading, an increase in biogas output was observed. It was observed that the amount of biogas produced in standard liters/day [Nl/d] coincided with the theoretical gas production in standard liters/day [Nl/d] or there was increased gas production compared with the theoretical gas production.

The volumetric loading of the plant could be increased further as a result of addition of *Clostridium sporosphaeroides* SBG3. The percentage content of dry matter and/or organic dry matter remained almost constant. This observation suggests that during fermentation of the fermentation substrate, no accumulation of nonfermented organic dry matter takes place. The addition of pure cultures of *Clostridium sporosphaeroides* SBG3 thus contributes to a continuous reaction of the dry matter contained in the fermentation substrate, which once again leads to continuous fermentation, since the accumulation of dry matter is reduced.

In phases in which the biogas plant is operated at constant volumetric loading, even a decrease of dry matter is observed, so that it can be concluded that the microorganisms *Clostridium sporosphaeroides* SBG3, with their hydrolytic metabolic activity, not only reduce the accumulation of dry matter in the fermenter, but also improve the hydrolytic reaction of this dry matter.

In the examples of application described, both pure cultures of *Clostridium sporosphaeroides* and mixed cultures with a proportion of *Clostridium sporosphaeroides* were used. In particular, mixed cultures of two or three species of microorganisms, selected from the group comprising *Paenibacillus macerans*, *Clostridium sartagoformum* and *Clostridium sporosphaeroides*, can be added.

Addition of the hydrolytically active, fermentative microorganism *Clostridium sporosphaeroides* SBG3 shows a beneficial effect on the hydrolysis of organic dry matter. By adding microorganisms of the species *Clostridium sporosphaeroides*, in otherwise identical conditions the volumetric loading of a fermenter can be increased about 4-5 kgoDM/m$^3$d to about 6 to 9 kgoDM/m$^3$d, without the slightest sign of instability of the fermentation process. In parallel with the increased volumetric loading, the amount of biogas formed is greatly increased. Furthermore, the specific yield of biogas increases, as far more of the organic dry matter is degraded than without addition of microorganisms of the species *Clostridium sporosphaeroides*. The use of microorganisms of the species *Clostridium sporosphaeroides* leads to a dramatic improvement in operational efficiency of biogas installations.

What is claimed is:

1. A method of improving the production of biomethane, comprising the step of adding a microorganism of the species *Clostridium sporosphaeroides* in a form of a culture of microorganisms to a biomass, with the microorganism of the species *Clostridium sporosphaeroides* accounting for at least 1% of the total number of microorganisms present in the culture, thereby enhancing a production of the biomethane in the biomass.

2. The method according to claim 1, wherein the *C. sporosphaeroides* liquefies the biomass.

3. The method according to claim 1, wherein, in the culture of microorganisms, the microorganism of the species *Clostridium sporosphaeroides* accounts for at least 10% of the total number of microorganisms present in the culture.

4. The method according to claim 1, wherein a pure culture of the microorganism of the species *Clostridium sporosphaeroides* is added.

5. The method according to claim 1, wherein the microorganism of the species *Clostridium sporosphaeroides* is added to the biomass as a constituent of at least one immobilized culture of microorganisms.

6. The method according to claim 1, wherein, at about the same time as addition of the microorganism of the species *Clostridium sporosphaeroides*, an additional biomass is added to the fermentation reactor, and the volumetric loading in the fermentation reactor is increased continuously by continuous addition of biomass.

7. The method according to claim 1, wherein the production of biomethane from biomass is carried out at a volumetric loading of ≧0.5 kgoDM/$m^3$d.

8. The method according to claim 1, wherein one or more microorganisms of the species *Clostridium sartagoformum* are added.

9. The method according to claim 8, wherein the microorganism is the strain *Clostridium sartagoformum* SBG1a, deposited under Biological Deposit No. DSM 22578.

10. The method according to claim 1, wherein one or more microorganisms of the species *Paenibacillus macerans* are added.

11. The method according to claim 8, wherein the microorganism is the strain *Paenibacillus macerans* SBG2.

12. A method of improving the production of biomethane, comprising the step of adding a microorganism of the species *Clostridium sporosphaeroides* in a form of a culture of microorganisms to a biomass, with the microorganism of the species *Clostridium sporosphaeroides* accounting for between $10^{-4}$% and 10% of the total number of microorganisms present in the culture, thereby enhancing production of biomethane in the biomass.

13. A method of improving the production of biomethane, comprising the step of adding a microorganism of the species *Clostridium sporosphaeroides* in a form of a culture of microorganisms to a biomass, with the microorganism of the species *Clostridium sporosphaeroides* accounting for between $10^{-3}$% and 1% of the total number of microorganisms present in the culture, thereby enhancing production of biomethane in the biomass.

* * * * *

```
                              SEQUENCE LISTING

<160> NUMBER OF SEQ ID NOS: 1

<210> SEQ ID NO 1
<211> LENGTH: 1409
<212> TYPE: DNA
<213> ORGANISM: Clostridium Sporosphaeroides SBG3

<400> SEQUENCE: 1
cagatcacct tagacacgtc cccttgcgg ttagactatt ggcttcgggt attaccggct      60
cccatggtgt gacgggcggt gtgtaccagg cccgggaacg tattcaccgc ggcatgatga    120
tccgcgatta ctagcaattc caacttcatg taggcgggtt gcagcctaca atccgaactg    180
agatcgcttt tgggggtttg ctccacctcg cggcttggct tccctctgtt agcgaccatt    240
gtagtacgtg tgtagcccag gtcataaggg gcatgatgat ttgacgtcgt ccccaccttc    300
ctccgttttg tcaacggcag tctgattaga gtgctcttgc gtacgactaa tcacaagggt    360
tgcgctcgtt gcgggactta acccaacatc tcacgacacg agctgacgac aaccatgcac    420
cacctgtctc aactttcccc gaagccacct aatgcatctc tgcctcgtta gttggatgtc    480
aagacctggt aaggttcttc gcgttgcttc gaattaaacc acatactcca ctgcttgtgc    540
gggcccccgt caattccttt gagtttcaac ctggcggccg tactccccag gtggatcact    600
tattgtgtta actccggcac ggaaggggtc agacccccca cacctagtaa tcatcgttta    660
cggcatggac taccagcgta tctaatcctg tttgctaccc aggcttccgt gcctcagcgt    720
cagttaaagc ccagtaggcc gccttcgcca ctggtgttcc tcccgatctc tacgcatttc    780
aacgctacac cgggaattcc gcctacatct acgtcaatca agcctcccag tttcgaacgc    840
aatttgtggg ttaagcccac agctctcacg cccgacttaa aaagccgcta cgcacccttt    900
acacccagta aatccggaca acgcttgctc cctacgtatt accgcggctg ctggcacgta    960
gttagccgga gcttcctcct tggctaccgt cattatcttc accaaggaca gaggtttaca   1020
atccgaagac cgtcttccct cacgcggcat tgctgcatca gagtttcctc cattgtgcaa   1080
tatcccccac tgctgcctcc cgtaggagtc tgggccgtgt ctcagtccca atgtggccgt   1140
tcagtctctc aacccggcta ccgatcgtcg ctttggtggg cctttacccc gccaactggc   1200
taatcggacg cgagtccatc tttcagcgga ttgctccttt gataccaagg ccatgcgacc   1260
ccaatatatc atgcggtatt agcgttcttt tcagaacgtt atccccctct gaaaggcagg   1320
ttactcacgc gttactcacc cgtccgccac taagtaagag ctaagcaagc ttctctcttc   1380
tccgtcgact tgcattttga acgtcgcga                                     1409
```